US005529055A

United States Patent [19]

Gueret

[11] Patent Number: 5,529,055

[45] Date of Patent: Jun. 25, 1996

[54] PIEZOELECTRIC NEBULIZING APPARATUS

[75] Inventor: Jean-Louis H. Gueret, Paris, France

[73] Assignee: L'Oreal, Paris, France

[21] Appl. No.: 250,474

[22] Filed: May 27, 1994

[30] Foreign Application Priority Data

Jun. 2, 1993 [FR] France .................................... 93 06561

[51] Int. Cl.[6] .................................................... A61M 11/00

[52] U.S. Cl. ............................... 128/200.16; 128/200.23; 128/200.22; 128/204.13

[58] Field of Search ......................... 128/200.16, 200.18, 128/200.21, 203.12, 200.22, 200.23, 204.13

[56] References Cited

U.S. PATENT DOCUMENTS

| | | | |
|---|---|---|---|
| 3,812,854 | 5/1974 | Michaels | 128/200.16 |
| 3,970,250 | 7/1976 | Drews | 128/200.16 |
| 4,294,407 | 10/1981 | Riechl et al. | 128/200.16 |
| 4,301,093 | 11/1981 | Eck | 239/102.2 |
| 4,334,531 | 6/1982 | Reichl et al. . | |
| 4,366,105 | 12/1982 | Nowacki | 128/204.13 |
| 4,790,479 | 12/1988 | Matsumoto et al. | 128/200.16 |
| 4,877,989 | 10/1989 | Drews et al. | 128/200.16 |
| 5,134,993 | 8/1992 | van der Linden et al. | 128/200.16 |
| 5,152,456 | 10/1992 | Ross et al. | 128/200.16 |
| 5,261,601 | 11/1993 | Ross et al. | 128/200.16 |

FOREIGN PATENT DOCUMENTS

| | | | |
|---|---|---|---|
| 531640 | 12/1957 | Belgium . | |
| 111163 | 6/1984 | European Pat. Off. . | |
| 258637 | 3/1988 | European Pat. Off. . | |
| 373237 | 6/1990 | European Pat. Off. . | |
| 2459052 | 1/1981 | France . | |
| 9010469 | 9/1990 | WIPO | 128/200.22 |
| 9114468 | 10/1991 | WIPO | 128/200.18 |
| 91/16997 | 11/1991 | WIPO . | |

OTHER PUBLICATIONS

Patent Abstracts of Japan, vol. 16, No. 437, (C-0984) Sep. 11, 1992 and JP-A-04-150,968 (Koji Toda) May 25, 1992.

French Search Report dated Feb. 8, 1994.

*Primary Examiner*—Edgar S. Burr
*Assistant Examiner*—William J. Deane, Jr.
*Attorney, Agent, or Firm*—Staas & Halsey

[57] ABSTRACT

Apparatus for nebulizing a fluid product, including a nebulizing device having a diffusing vibrating member, a high-frequency generator for vibrating the diffusing vibrating member, an electrical supply for the generator, a reservoir for the fluid product removably mounted in the apparatus independently of the diffusing vibrating member, a member for supplying the diffusing vibrating member with liquid product, the supply member having an operating rod, a transfer piece and a flexible member capable of conveying the fluid product to the vibrating member, said flexible member being placed opposite the vibrating member, wherein a fluid communication is provided through the transfer piece, the operating rod and the flexible member.

14 Claims, 2 Drawing Sheets

PIEZOELECTRIC NEBULIZING APPARATUS

BACKGROUND OF THE INVENTION

Apparatuses are known for nebulizing a fluid product, including a nebulizing device a diffusing vibrating member, a high-frequency generator, an electrical supply for the generator, a reservoir for the fluid product, mounted in the apparatus in a removable manner and independently of the vibrating member, a means being provided for supplying the vibrating member with product, at least part of the supply means, such as a pump or a simple valve, being carried by the reservoir. Such a device is, for example, described in FR-A-2,459,052, with reference to its FIG. 1, and especially used in medical applications such as inhalers. According to this document a reservoir in two parts includes liquid pump and a single-way distributor, or, as a variant, a simple valve associated with a reservoir containing a gas keeping the liquid under pressure; the upper part of the reservoir includes a prolongation through which passes an outlet channel and, at the free end of the prolongation, a preparation member in the form of a concave cup partly covered by an upper baffle inclined towards the diffusing vibrating member, in this case the atomizing element in the form of a spraying plate, like that described on page 4, lines 19 to 39, of the document. Thus, the liquid product is projected on to the spraying plate by the supply means. Such an arrangement has the drawback that, in order to be sure that the liquid product reaches the spraying plate, it is necessary to provide complicated deflecting members, such as the concave cup and its upper baffle, these not always being easy to size and to position, especially if it is not desired for the liquid product to be also projected outside and around the spraying plate, this not only dirtying the apparatus but also leading to a consumption of unused liquid product, a consumption all the more regrettable especially when the nebulizing apparatus is of very small overall size so as to be easily transportable in a handbag or a pocket of a garment.

SUMMARY OF THE INVENTION

The object of the present invention is to produce a nebulizing apparatus not having these drawbacks.

According to the present invention, an apparatus for nebulizing a fluid product, including a nebulizing device includes a diffusing vibrating member, a high-frequency generator, an electrical supply intended for the generator, a reservoir for the fluid product to be nebulized, mounted in the apparatus in a removable manner and independently of the vibrating member, a means being provided for supplying the vibrating member with product, at least part of the supply means, such as a pump or a simple valve, being carried by the reservoir, wherein, the pump or the simple valve has an operating rod, a transfer piece carries, on the one hand, the operating rod and, on the other hand, a flexible member capable of conveying the fluid product on to the vibrating member and placed right opposite the latter, a communication being provided between the volumes of the transfer piece which are occupied by the operating rod and the flexible member.

The vibrating member includes a metal or ceramic plate; the plate may be solid or porous, or micropierced in the form of a grid. The plate may be in the form of a spherical or conical bowl; it may also be planar and arranged at any inclination in the nebulizing apparatus.

The fluid product to be nebulized is generally a liquid, for example a perfuming or treating, aqueous or aqueous/alcoholic composition; this may also be a gel, the viscosity of which, different from that of water or alcohol, makes it possible, in the case where the vibrating member is a plate in the form of a grid, to provide, in the grid, larger perforations than those necessary for a liquid product, through which the gel does not pass in the absence of vibrations. In addition, when the gel has thixotropic properties as soon as it is vibrated, it passes into a more fluid state and it is easier to nebulize.

Preferably, the apparatus includes a casing, a housing for mounting the reservoir in a removable manner, and a diffusion mouth.

Advantageously, the housing is bound by a wall having an opening through which passes the means for supplying the vibrating member with fluid product, an operating member being provided for the operation of the supply means.

Advantageously, the supply means is entirely carried by the reservoir and is therefore, like the latter, entirely removable; by virtue of this arrangement, since the setting into vibration of the diffusing vibrating member automatically cleans the latter, it is possible to use in succession, in the same apparatus, at least two different products: in the case of skin treatment, for example, two products may be applied in succession, even if the two products are rendered incompatible when they are put together for too long; in the case of a perfume especially, an evening perfume may be treated in the same apparatus as a daytime perfume without modification of the note of the evening perfume by that of the daytime one.

Advantageously, the reservoir is mounted so as to slide in the housing.

Preferably, the electrical supply is integral with the reservoir; the electrical supply is associated with an electrical contactor, one of the contacts of which is carried by the operating member; the casing has a receptacle for receiving a spare reservoir.

Preferably, the flexible member is a brush.

As a variant, the flexible member is a foam or a flexible elastic frit.

In another variant, the flexible member is a flocked foam or a flocked flexible elastomeric plastic.

According to another variant, the flexible member is in the form of a semi-flexible bellmouth with fringes prolonging the transfer piece.

Preferably, the reservoir is made of a rigid material, glass, ceramic or synthetic material.

As a variant, the reservoir is a flexible bag.

Advantageously, the vibrating member and the transfer piece are carried by the casing and the transfer piece passes through the opening in the wall of the casing, bearing on the wall.

Preferably, the vibrating member and the transfer piece are carried by the operating member housed in a cavity bordered by the wall equipped with the opening, the transfer piece passing through the opening, bearing on the wall.

BRIEF DESCRIPTION OF THE DRAWINGS

In order to make the object of the invention easier to understand, an embodiment thereof will now be described, by way of purely illustrative and non-limiting examples and represented in the appended drawings.

In these drawings.

DESCRIPTION OF THE PREFERRED EMBODIMENTS

Figure 1:
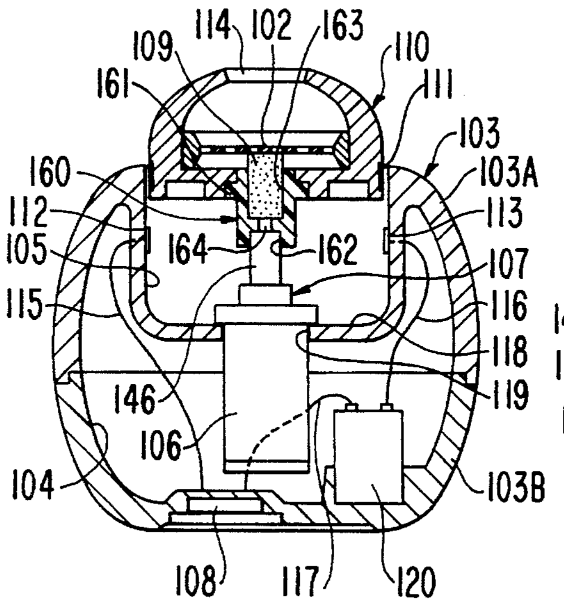
FIG. 1 is a diagrammatic sectional view of a nebulizing apparatus according to the invention.

Referring to FIG. 1, an apparatus for nebulizing a liquid according to the present invention includes a casing 103 having two shells joined together, an upper shell 103A and a lower shell 103B. The upper shell 103A defines a cylindrical cavity 105 emerging at its upper part and having a wall 118; the two shells 103A, 103B also define, beneath the cavity 105, a housing 104.

An operating member 110 includes a hollow push-button mounted so as to slide in the cavity 105. The push-button includes, on the one hand, a transverse bottom wall and, on the other hand, an opening 114 constituting a diffusion mouth for the nebulized product. A diffusing vibrating member is arranged, inside the operating member 110 in the vicinity of its bottom wall which carries a transfer piece 160; the perforations of the grid 102 are of micron size: for example, they have a diameter lying between 1 and 200 microns; they may be obtained e.g., chemically or by laser machining, the grid being a ceramic substance; the grid 102 constitutes a finely calibrated screen making it possible to receive a liquid product which is held in place by surface tension.

The transfer piece 160 passes through an opening made in the transverse wall of the operating member 110 and bears, by a flange 161, on the said wall; the transfer piece 160 includes two bores 162, 163 defining two volumes separated by a web but communicating via an orifice 164 made in the web.

According to this variant, a reservoir 106 a flexible bag, filled with liquid without air, and a supply means 107 includes a pump without uptake of air; this makes possible a use of the apparatus in all positions and, at the same time, better preservation of the liquid product, especially when this liquid is a perfume.

An operating rod 146 of the pump of the supply means 107 sits with its end in the bore 162, while the bore 163 receives a flexible member 109 having a capillary structure or felt, such as an open-cell foam for example, bearing on the grid 102, also forming part of the supply means.

A high-frequency generator 120, not detailed, is placed in the housing 104 as is an electrical supply 108 for this generator; a conductor 117 connects one pole of electrical supply 108 to a terminal of the generator; the other terminal of the generator 120 and the other pole of the supply 108 are connected respectively to contacts 112, 113 carried by the inner wall of the cavity 105, via conductors 115, 116; the operating member 110 carries, on its periphery, a conducting ring 111.

The operation of the nebulizing apparatus which has just been described is as follows.

The reservoir 106 has been filled beforehand with a liquid to be nebulized; this liquid could be, for example, a perfume, a toilet water, a face-care product or another product.

When the user desires to nebulize the liquid contained in the reservoir 106 mounted beforehand in a circular opening 119 made in the bottom of the wall 118 which forms part of the cavity 105, he exerts an action on the operating member 110 which is transmitted, via the transfer piece 160, to the operating rod 146 of the pump of the supply means 107 bearing on the wall 118, and liquid is sent via the pump of the supply means 107 on to the grid 102 through the flexible member 109 such as felt; in parallel, the ring 111 arrives right opposite the contacts 112 and 113 and the generator 120 is supplied electrically; setting the grid 102 into vibration gives rise to a cloud of extremely fine liquid particles, their sizes being of the order of 0.2 to 15 microns in diameter. Such a cloud, emitted at the outlet of the casing 103 via the opening 114, has the advantage of not being wet and is therefore beneficial for applications such as cosmetics, or pharmaceuticals. It will also be noted that the nebulizing apparatus according to the invention, which discharges the cloud of liquid particles having passed through the grid 102, makes it possible for the latter to remain clean after use and therefore to be able to replace a first reservoir containing a first liquid with a second reservoir containing a second liquid, different from the first, without the second liquid being contaminated by the first; this is especially advantageous in cosmetics when the liquids are perfumes. These various reservoirs constitute as it were refills for the apparatus; it is possible, according to a variant not shown, to arrange the casing 103 so as to have a receptacle receiving a spare reservoir equipped with a felt protected by a cap and containing the same liquid or a liquid different from that of the reservoir 106; having a capacity of from 2 to 5 milliliters of liquid, such reservoirs lead to nebulizing apparatuses of very small overall size, which can be easily transported in a handbag, or a pocket of a garment. Moreover, such an apparatus has the advantage of being able to be used in any position whatsoever.

Figure 2:
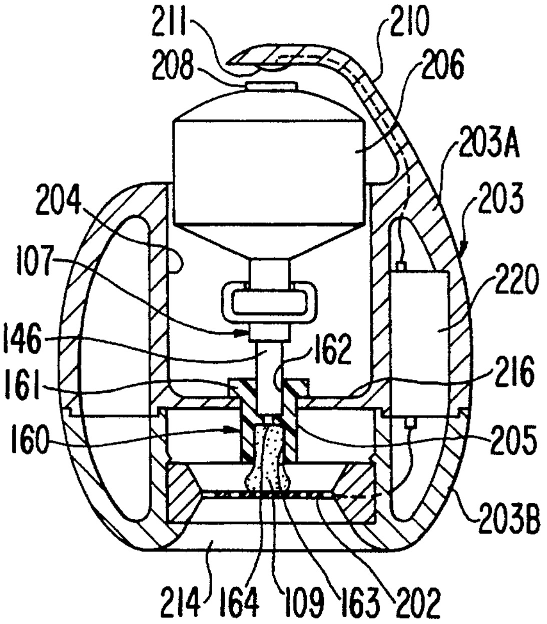
FIG. 2 is a diagrammatic sectional view of a variant of a nebulizing apparatus according to the invention.

According to the variant of FIG. 2, the casing 203 includes two shells 203A, 203B; the supply means 107 includes a pump having an operating rod 146 received in a bore 162 of a transfer piece 160; the transfer piece 160 has another bore 163 receiving a flexible member 109 such as felt, the bores 162 and 163 communicating via an orifice 164; a flange 161 of the transfer piece 160 enables the latter to bear on the wall 216 of the housing 204 provided in the shell 203A passing through the circular opening 205. The pump of the supply means 107 is carried by a reservoir 206, the bottom of which supports, on the outside, the electrical supply 208 for a generator 220 housed in the shell 203A. An operating member 210 in the form of a flexible lever carries a contact 211 for closing the electrical supply circuit of the generator 220; a grid 202 enables liquid to be nebulized through the diffusion mouth 214 made at the lower part of the shell 203B.

Figure 3:
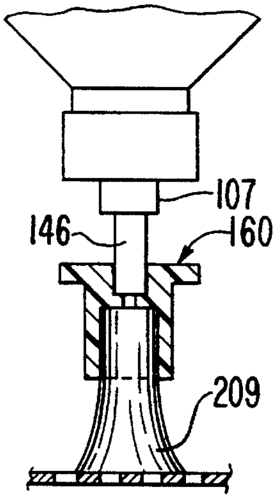
FIGS. 3 to 6 show various forms of flexible members.
Figure 4:
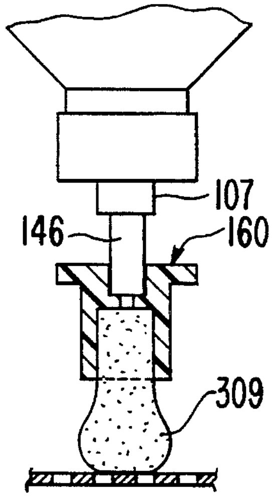
Figure 5:
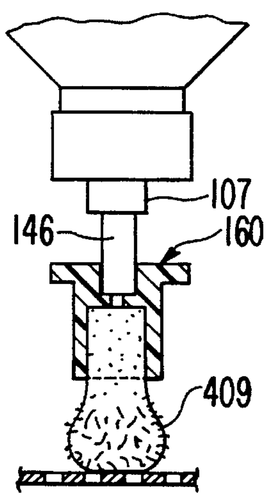
Figure 6:
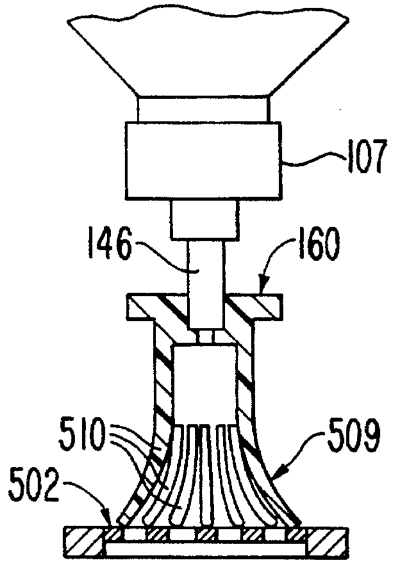

FIGS. 3 to 6 show embodiment variants of flexible members associated with the transfer piece 160 carrying the operating rod 146 of the pump of the supply means 107; according to FIG. 3, the flexible member 209 is a brush having bristles whose length and/or composition and/or size of the cross-section would make it possible to regulate the flow rate of liquid; according to FIG. 4, the flexible member 309 is made of cotton or made of, polyurethane or polyether open-cell foam; it may also be a frit of elastomer or of polyethylene; according to FIG. 5, the flexible member 409 is flocked, whether it is made of foam or made of flexible elastomeric plastic frit. According to FIG. 6, the flexible member 509 is more suited to the supply of the vibrating member 502 when the product is a gel; the flexible member 509 includes a kind of semi-flexible bellmouth 510 with fringes, prolonging the transfer piece 160; it will be noted that the vibrating member 502, in the form of a metal disc, has larger perforations than those of FIGS. 3 to 5 which are more suited to a liquid product.

Figure 7:
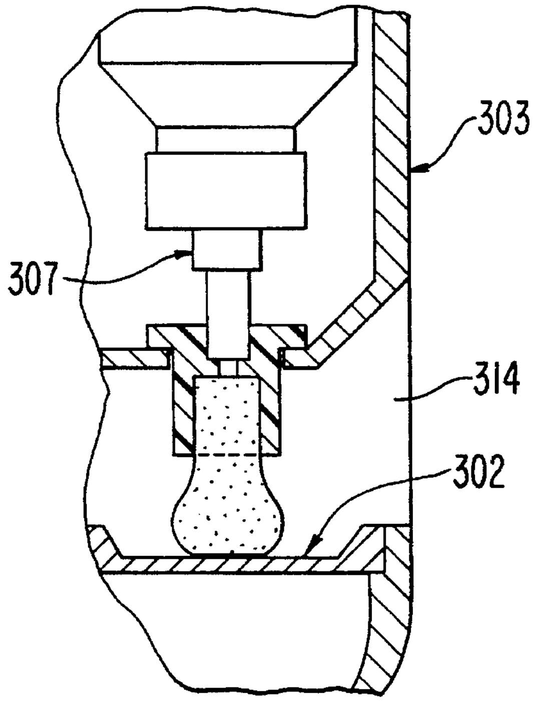
FIG. 7 shows, partially, a variant of an apparatus whose vibrating member is devoid of perforations.

FIG. 7 shows an example of an apparatus whose vibrating member 302 is an opaque ceramic which is non-porous and has no hole; the casing 303 has a lateral diffusion mouth 314 placed, with respect to FIG. 7, at the top of the vibrating member 302; the nebulized particles land on the vibrating member 302 and pass through the diffusion mouth 314. According to this example too, the supply means 307 includes a simple valve.

Figure 8:
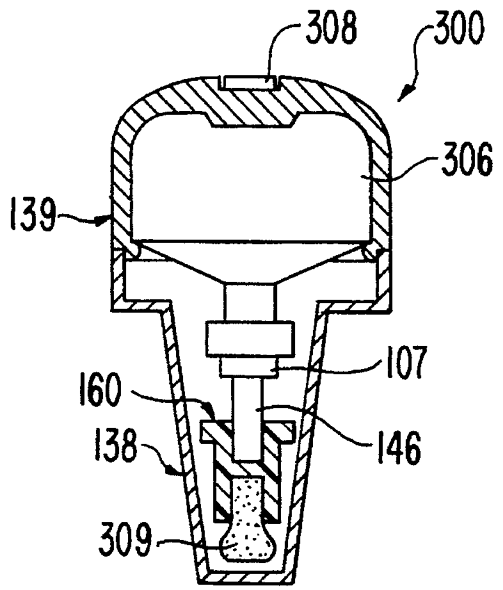
FIG. 8 represents a refill intended for an apparatus according to the invention.

FIG. 8 shows a reservoir 306 equipped with the supply means of FIG. 4; the reservoir 306, which may be made of glass, is protected by an envelope 139 on to which is clipped a cap 138 for protecting the supply means, the assembly constituting a storable refill 300; according to the example shown in this figure, the electrical supply 308 is carried by the envelope 139.

I claim:

1. Apparatus for nebulizing a fluid product, comprising:

a) a housing; and b) an electrically actuated nebulizing device connected to the housing, the nebulizing device including
   1) an electrical supply,
   2) a high frequency vibration generator electrically connected to the electrical supply,
   3) a diffusing vibrating member,
   4) a switch electrically connecting the electrical supply, the generator, and the diffusing vibrating member,
   5) a reservoir containing the fluid product and being mounted in the housing in a removable manner independently of the diffusing vibrating member,
   6) a fluid product supply member connecting the reservoir and the diffusing vibrating member for supplying the diffusing vibrating member with the fluid product from the reservoir, wherein the supply member is selected from the group comprising a pump or valve connected to the reservoir and has an operating rod connected to the pump or valve, a transfer piece connected to the operating rod, and a flexible member connected to the transfer piece for conveying the fluid product to the diffusing vibrating member, said flexible member being placed opposite the diffusing vibrating member, and wherein a fluid communication is provided through the transfer piece, the operating rod and the flexible member; and
   7) a manually operable activator connected to the housing and operable for simultaneously activating the switch for turning the nebulizing device on and the supply member to cause fluid product to be supplied from the reservoir to the diffusing vibrating member.

2. Apparatus according to claim 1, wherein the diffusing vibrating member is a grid.

3. Apparatus according to claim 2, further comprising a housing for mounting the reservoir and having a diffusion mouth, wherein the housing is bound by a wall having an opening for receiving the supply member and an operating member provided for the operation of the supply member.

4. Apparatus according to claim 3, wherein the reservoir is slidably mounted in the housing.

5. Apparatus according to claim 1, wherein the electrical supply is integral with the reservoir.

6. Apparatus according to claim 3, wherein the electrical supply is associated with an electrical contact on the operating member.

7. Apparatus according to claim 3, wherein the diffusing vibrating member and the transfer piece are located on the housing and the transfer piece passes through an opening in a wall of the housing, bearing on the wall.

8. Apparatus according to claim 3, wherein the vibrating member and the transfer piece are located on the operating member housed in a cavity bordered by a wall equipped with an opening, the transfer piece passing through the opening, bearing on the wall.

9. Apparatus according to claim 1, wherein the flexible member is a brush.

10. Apparatus according to claim 1, wherein the flexible member is one of a foam and a flexible elastic frit.

11. Apparatus according to claim 1, wherein the flexible member is one of a flocked foam and a flocked flexible elastomeric plastic.

12. Apparatus according to claim 1, wherein the flexible member is a semi-flexible bellmouth with fringes, and is an extension of the transfer piece.

13. Apparatus according to claim 1, wherein the reservoir is made of a rigid material.

14. Apparatus according to claim 1, wherein the reservoir is a flexible material.

* * * * *